(12) United States Patent
Beekmans

(10) Patent No.: US 8,951,043 B2
(45) Date of Patent: Feb. 10, 2015

(54) INSERTION PART OF A TWO-PART IMPLANT WITH INSERTION INSTRUMENT

(75) Inventor: Rembardinus Beekmans, Amsterdam (NL)

(73) Assignee: White Implants Development Corp., Amsterdam (NL)

( * ) Notice: Subject to any disclaimer, the term of this patent is extended or adjusted under 35 U.S.C. 154(b) by 0 days.

(21) Appl. No.: 13/127,824

(22) PCT Filed: Nov. 2, 2009

(86) PCT No.: PCT/NL2009/000207
§ 371 (c)(1),
(2), (4) Date: May 5, 2011

(87) PCT Pub. No.: WO2010/053352
PCT Pub. Date: May 14, 2010

(65) Prior Publication Data
US 2011/0212417 A1    Sep. 1, 2011

(30) Foreign Application Priority Data

Nov. 5, 2008   (NL) ...................................... 1036155

(51) Int. Cl.
*A61C 8/00*         (2006.01)

(52) U.S. Cl.
CPC .............. *A61C 8/0089* (2013.01); *A61C 8/0022* (2013.01); *A61C 8/0018* (2013.01)
USPC .......................................... 433/174; 433/173

(58) Field of Classification Search
CPC ........................................... A61C 8/00–8/0098
USPC .................... 433/172–176, 201.1; 623/17.17; 606/300–320, 86 A, 86 R, 104, 232; 81/124.2, 124.3, 176.15; 411/402; 403/57, 58, 61
See application file for complete search history.

(56) References Cited

U.S. PATENT DOCUMENTS 5,358,529 A * 10/1994 Davidson .................... 623/20.19
5,816,812 A * 10/1998 Kownacki et al. ............ 433/174
(Continued)

FOREIGN PATENT DOCUMENTS

| ES | 2278477 A1 | * | 7/2004 |
| ES | 2278477 | * | 8/2007 |
| WO | 2004 075769 | | 9/2004 |

OTHER PUBLICATIONS

International Search Report issued Mar. 16, 2010 in PCT/NL09/000207 filed Nov. 2, 2009.

(Continued)

*Primary Examiner* — Edward Moran
(74) *Attorney, Agent, or Firm* — Oblon, Spivak, McClelland, Maier & Neustadt, L.L.P.

(57) ABSTRACT

The invention provides a method for inserting an insertion part of a two-part zirconium-like implant into the jawbone at high force without breaking in order in this way to increase the primary stability of the implant in the jawbone. This is made possible by providing an insertion part at the outside of two or more protrusions at the level of the jawbone line over which an insertion instrument with recesses fits which engages these protrusions in order to subsequently insert the insertion part into the jawbone. The sleeve-shaped insertion instrument with the recesses and the neck of the insertion part with the two or more protrusions can be shaped in such a way that they fit precisely together or that a connection resembling a cardan coupling is produced, so that the implantologist can hold the insertion instrument in various positions above the insertion part while the desired direction of insertion is still maintained.

5 Claims, 4 Drawing Sheets

(56) References Cited

U.S. PATENT DOCUMENTS

| | | | |
|---|---|---|---|
| 6,247,932 B1* | 6/2001 | Sutter | 433/173 |
| 6,416,324 B1 | 7/2002 | Day | |
| 6,488,501 B1* | 12/2002 | Harding | 433/173 |
| 7,104,797 B2* | 9/2006 | Rassoli | 433/173 |
| 2002/0150862 A1 | 10/2002 | Day | |
| 2004/0029075 A1* | 2/2004 | Peltier et al. | 433/173 |
| 2004/0033469 A1* | 2/2004 | Blacklock | 433/173 |
| 2006/0078847 A1* | 4/2006 | Kwan | 433/174 |
| 2008/0032263 A1 | 2/2008 | Bondar | |
| 2009/0202962 A1* | 8/2009 | Xam-Mar Mangrane | 433/173 |

OTHER PUBLICATIONS

Y. Ichikawa et al., "Tissue Compatibility and Stability of a New Zirconia Ceramic in Vivo", Journal of Prosthetic Dentistry, Aug. 1992, vol. 68, No. 2, pp. 322-326 (in English).

H. Warashina et al., "Biological Reaction to Alumina, Zirconia, Titanium and Polyethylene Particles Implanted onto Murine Calvaria", Biomaterials, 2003, 24, pp. 3655-3661 (in English).

M. Andreiotelli et al., "Survival Rate and Fracture Resistance of Zirconium Dioxide Implants After Exposure to the Artificial Mouth: An In-Vitro Study", Inaugural Dissertation, Freiburg, 2006 (in English).

J. Oliva et al., "One-Year Follow-Up of First Consecutive 100 Zirconia Dental Implants in Humans: A Comparison of 2 Different Rough Surfaces", International Journal of Oral Maxillofac Implants, 2007, vol. 22, No. 3, pp. 430-435 (in English).

A. Rabel et al., "Clinical Study on the Primary Stability of Two Dental Implant Systems with Resonance Frequency Analysis", Clinical Oral Investigations, Sep. 2007, vol. 11, No. 3, pp. 257-265 (in English).

C.K. Ho, "Immediate Function with Dental Implants" Dental Practice, Mar./Apr. 2005, pp. 156-166 (in English).

* cited by examiner

INSERTION PART OF A TWO-PART IMPLANT WITH INSERTION INSTRUMENT

CROSS REFERENCE TO RELATED APPLICATION

This application is a National Stage of PCT/NL09/000,207, filed on Nov. 2, 2009, which claims priority to The Netherlands Patent Application No. 1036155, filed Nov. 5, 2008. The contents of this document are incorporated herein by reference.

TECHNICAL FIELD

The embodiments herein relate to a dental implant system.

BACKGROUND

In dentistry, implants are used to replace missing teeth elements. This is carried out by drilling a cavity into the jawbone into which the implant is securely screwed or pressed. A dental prosthesis or crown is subsequently placed on the part of the implant that protrudes above the gums. Implants made of titanium have long yielded excellent results as far as durability and reliability are concerned. A drawback of using titanium implants, which are grey in colour, is the fact that titanium implants in many cases show through at the front on account of the edge of the bone which is locally thin there. Metallic edges also in many cases become visible over the course of time at the level of the line dividing the crown from the implant. In addition, research indicates that ceramic particles cause less inflammation and bone resorption than titanium particles; see Ichikawa Y., Akagawa Y., Nikai H., Tsura H., Tissue comptability and stability of a new zirconia ceramic in vivo, Journal of Prosthetic Dentistry 1992:68:322-326 and Warashina H., Sakano S., Kitamura S. et al., Biological reaction to aluminia, zirconia, titanium and polyethylene particles implanted onto murine calvaria, Biomaterials 2003: 24:3655-3661. In order to eliminate these drawbacks of the often disappointing aesthetics and to utilize the advantages of better biocompatibility of ceramic, implants made of zirconium oxide have been developed. The current-day zirconium material has a high bending force (900-1,200 MPa), a Vickers hardness of (1,200) and a Weibull modulus of (10-12), making it a suitable material to make dental implants from. See for example "Survival rate and fracture resistance of zirconium dioxide implants after exposure to the artificial mouth": An in-vitro study, inaugural dissertation Freiburg 2006, Andreiotelli M. and Oliva J., Oliva X., Oliva J D, One year follow-up of first consecutive 100 zirconia dental implants in humans: A comparison of 2 different rough surfaces, Int. J. Oral Maxillofac Implants 2007:22:430-435. There are currently various commercially available zirconium oxide implants which have to date been one-part implants such as Z-look3® and Sigma®.

However, just as in titanium implants, developments in zirconium oxide implants are tending toward two-part implants. A two-part implant allows the practitioner to choose. If the quality of the jawbone allows an insertion force of greater than 45 Ncm, the implant has sufficient primary stability to load it directly with a construction and a temporary arrangement. This is very important for patients on account of the aesthetic aspect in the replacement of front teeth. See in this regard example: "Clinical study on the primary stability of two dental implant systems with resonance frequency analysis", Rabel, Annette1; Köhler, Steffen; Schmidt-Westhausen, Andrea, Clinical Oral Investigations, Volume 11, Number 3, September 2007 and "Immediate function with dental implants, Ho, C. C. K, Dental Practice, March/April 2005". If this is not the case, then the loading can be delayed until the moment that the insertion part, covered by the gums, has first grown sufficiently together with the jawbone, that is to say is sufficiently osseointegrated. The force (Ncm) at which the implant can be brought into the jawbone is, beside good jawbone quality, very important. Now, a problem with zirconium oxide implants is the brittle material which soon breaks in the case of an excessively high force and/or in the case of a disadvantageously distributed force.

Two-part titanium implants are brought into the jawbone by means of an insertion instrument which is fed into the cavity of the insertion part. The insertion instrument can in this case be operated manually or else be clamped in a drilling machine. See in this regard for example the insertion instruments and the way in which the insertion parts are thus brought into the jawbone in the case of known two-part titanium implants for example Biomet 3i®, Nobel Biocare® and Straumann®. However, in the case of a zirconium-like insertion part, in particular in the case of insertion parts which have a cross section of 4 mm or less and are often used in the thin jawbone when replacing front teeth, the force which is exerted with an insertion instrument which is fed into the cavity is very soon too high. That is to say, the thin walls of a zirconium-like insertion part are unable to withstand, or have difficulty withstanding without breaking, the outwardly directed force which is for example greater than 30 Ncm. Furthermore, if the implantologist does not secure the instrument in an optimum position, i.e. perpendicularly above the insertion part, during the insertion, the force is increased still further as a result of the leverage and also distributed disadvantageously over the walls of the insertion part, as a result of which the insertion part breaks at the level of the neck. Premature breaking during the insertion of an implant is much less common in one-part zirconium-like implants because such implants are not internally hollow or weakened by a different connecting geometry. These implants are brought into the jawbone by means of an all-encompassing sleeve-like instrument; this is slid over the implant.

SUMMARY

The present invention relates to an insertion part of a two-part zirconium dental implant with at the outside 2 or more protrusions and an insertion instrument with recesses which can thereby engage the protrusions in order to insert the insertion part in this way into the jawbone. The design of both the insertion instrument and the insertion part and also the way in which the insertion instrument engages the insertion part ensures that the insertion part can be brought into the jawbone at a high force of for example more than 30 Ncm without breaking. Even if the insertion instrument is not positioned optimally on the insertion part, the insertion part can be brought into the jawbone at this force without breaking.

Now, the invention provides a method for inserting a zirconium-like insertion part of a two-part implant into the jawbone at a high force of for example more than 30 Ncm. This is made possible by providing the insertion part with two or more protrusions at the outside which can be engaged by an insertion instrument with recesses in order in this way to bring the insertion part into the jawbone. The protrusions may be located anywhere at the outside of the insertion part. However, preferably, the protrusions are located at a site of the insertion part where the connection to the construction and/or carrier part is not located, because the insertion part is thickest and as a result strongest at that location. Preferably, the protrusions are located just above the jawbone line of the insertion part, as a result of which the osseointegration is not disturbed and the patient is not prevented from practising good oral hygiene. As far as the outsides of the protrusions are concerned, preference is given to an arched design and, as far as the upper rim of the outsides is concerned, to an organic shape such as for example globular. As a result, zirconium-like protrusions will crumble away less rapidly.

Furthermore, the protrusions at the outside of the insertion part and the recesses of the insertion instrument which fit thereover may be shaped in a broad range of ways. Preference is given to an embodiment wherein the protrusions of the insertion part are round or oval-shaped which fit into the recesses of an insertion instrument which in a preferred embodiment are semicircular at the upper rim. This allows the protrusions to be engaged in a sliding manner by the insertion instrument, as a result of which the implantologist can secure the insertion instrument in more positions while the desired direction of insertion of the insertion part into the jawbone is still maintained.

The insertion instrument with the recesses can in one embodiment be made suitable for clamping in a machine, which is used to bring the insertion part into the jawbone, but can also in one embodiment be made suitable as a hand-held instrument. The insertion instrument with recesses can also be shaped in a broad range of ways. A preferred embodiment of the insertion instrument is for the upper rim to be sleeve-shaped and for the sleeve-shaped upper rim to fit on the neck of the insertion part. If the neck of the insertion part with the protrusions is straight-shaped and the sleeve-shaped insertion instrument with the recesses fits precisely thereover here, the implantologist is forced to hold the insertion instrument perpendicularly on the insertion part, making it more clearly apparent up to what point the implantologist must bring the insertion part into the jawbone.

In another preferred embodiment of the insertion part with protrusions, the neck of the insertion part is shaped somewhat spherically, so that a connection resembling a cardan coupling is produced during the placing of the sleeve-shaped insertion instrument on the protrusions of the insertion part. This way, resembling a cardan coupling, of engaging allows the insertion part, even if the insertion instrument is not being held in the optimum position, i.e. perpendicularly above the insertion part, nevertheless to be brought into the jawbone in the desired direction of insertion. In a preferred embodiment, the upper edge of the neck of the insertion part is rounded-off.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings. However, the accompanying drawings and their exemplary depictions do not in any way limit the scope of the inventions embraced by this specification. The scope of the inventions embraced by the specification and drawings are defined by the words of the accompanying claims.

DETAILED DESCRIPTION

Figure 1:
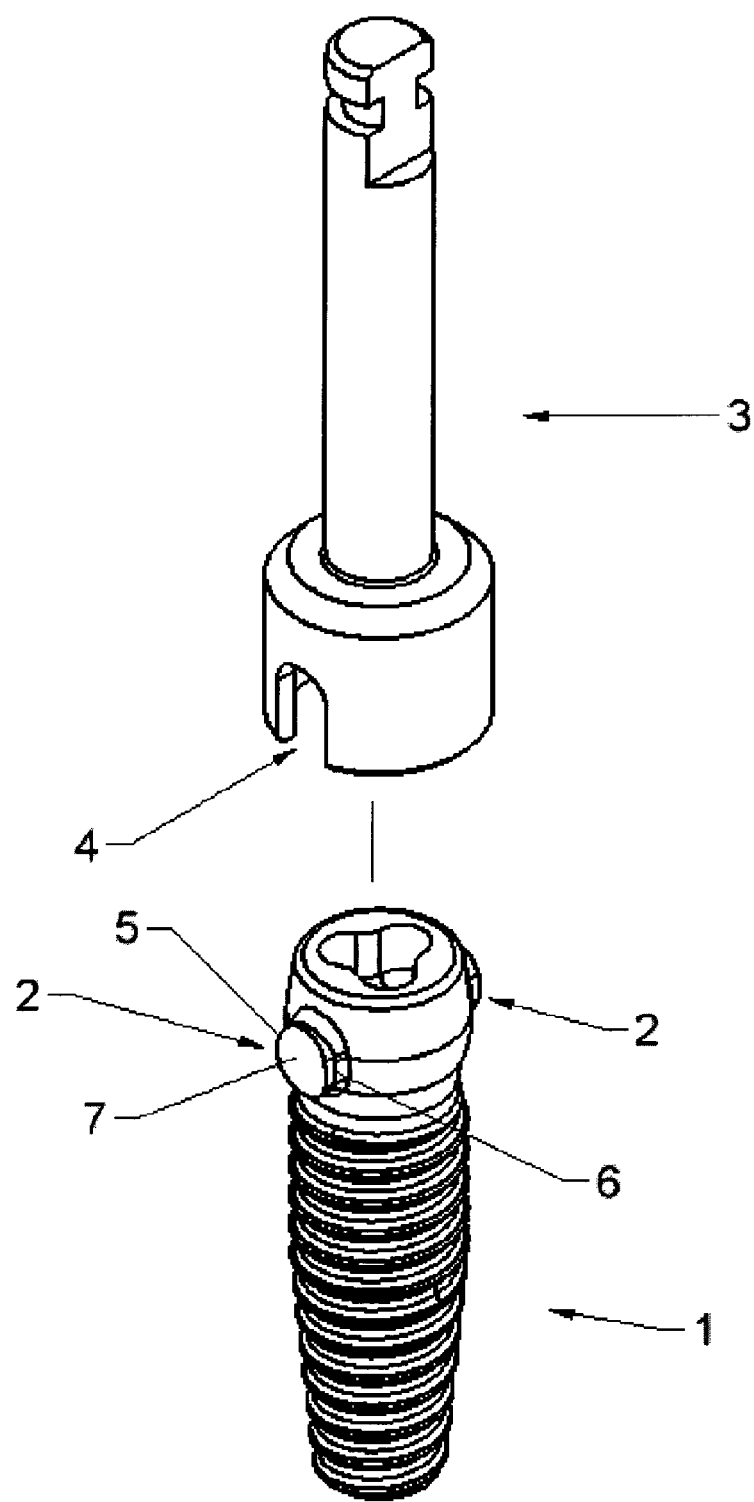
FIG. 1 is a perspective view drawing of an insertion part and an insertion tool according to an exemplary embodiment of the present disclosure.
Figure 2:
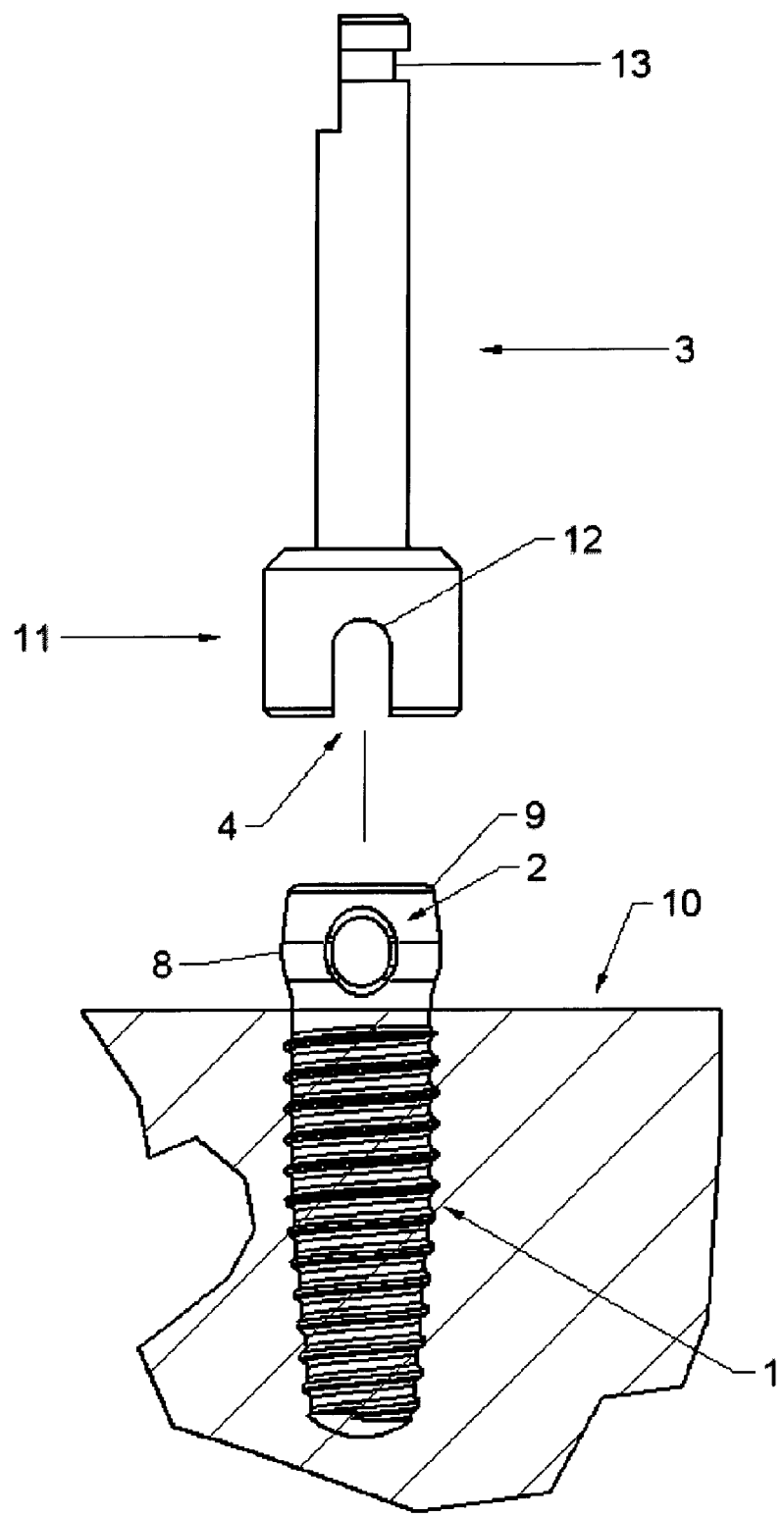
FIG. 2 is an exploded side view drawing of the insertion part implanted in a jawbone and the insertion tool according to the exemplary embodiment of FIG. 1.
Figure 3:
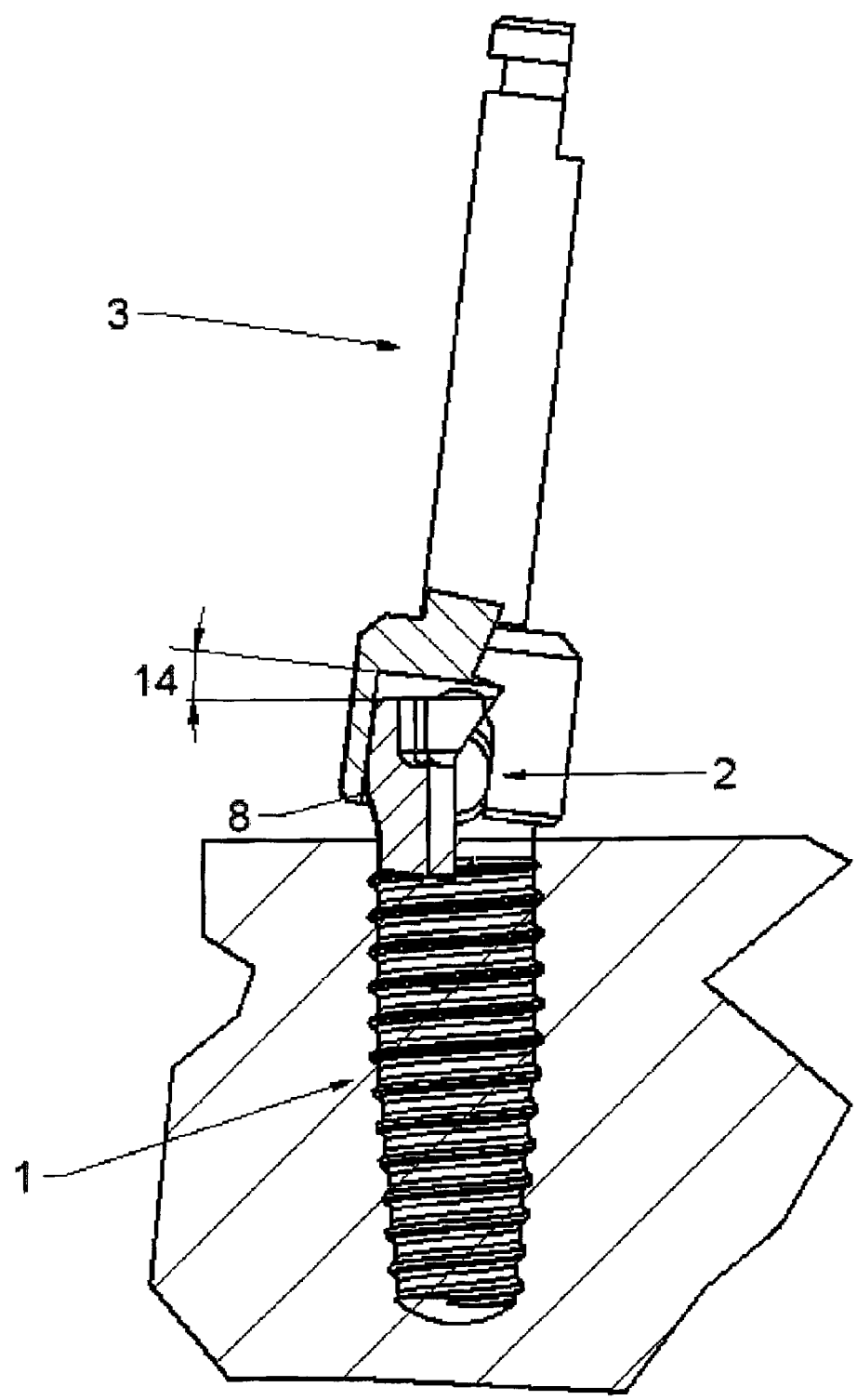
FIG. 3 is a side view drawing and partial cross-sectional view of the insertion part implanted in a jawbone and the insertion tool connected with the insertion part according to the exemplary embodiment of FIG. 1.
Figure 4:
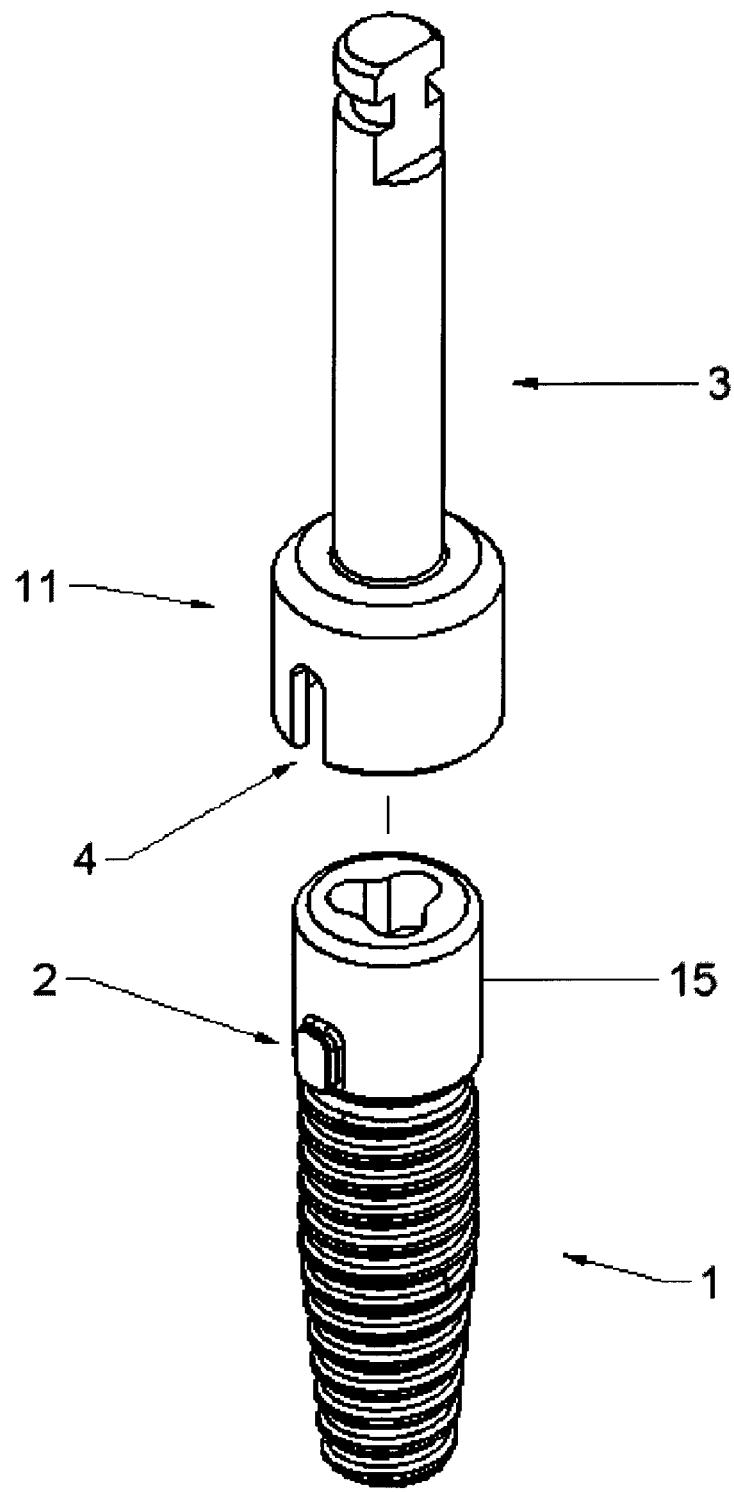
FIG. 4 is a perspective view drawing of an insertion part and an insertion tool according to another exemplary embodiment of the present disclosure.

FIG. 1 shows an insertion part (1) with protrusions (2) which are round and/or oval-shaped (5) and of which the outsides are arched (6) and the upper rim is globular (7) with thereabove an insertion instrument (3) to be placed thereon with recesses (4). FIG. 2 shows a annular spherically shaped neck (8), having a diameter and height, of the insertion part (1) with a rounded-off upper edge (9) and a protrusion (2) just above the jawbone line (10). Thereabove a sleeve-shaped (11) insertion instrument (3) with recesses (4) which are semicircular (12) at the upper rim and which has on the stem a notch (13) which serves for clamping in a machine. FIG. 3 shows an insertion instrument (3) placed on an insertion part (1) with a protrusion (2) which is partially cut away. The spherically shaped neck (8) and the connection (14) resembling a cardan coupling are shown here. FIG. 4 shows an insertion part (1) with one of the protrusions (2), the neck being straight-shaped (15) with thereabove a fitting sleeve-shaped (11) insertion instrument (3) which is to be placed thereon with one of the recesses (4).

The invention claimed is:

1. A two part dental implant insertion system, comprising; a threaded zirconia insertion part adapted to be implanted in the jawbone, the insertion part being able to withstand an insertion force of at least 30 N-cm; and an insertion instrument for inserting the insertion part into the jawbone, wherein the insertion part includes a neck adapted to protrude above the jawbone, the neck including two or more round or oval protrusions disposed on a lower end of an outside wall of the neck, the neck including an annular segment having a curved profile, the curved profile corresponding in shape to an annular segment of a sphere and being disposed around the neck such that a diameter of the annular segment is more narrow at an insertion side of the insertion part than a diameter of the annular segment at an insertion instrument connection side of the insertion part, wherein the protrusions extend across an entirety of a height of the annular segment; wherein the insertion instrument includes a sleeve shaped upper rim that fits over the neck of the insertion part, the upper rim having recesses which are semi-circular for a fitting connection with the round or oval protrusions of the insertion part; and wherein the fitting connection between the insertion part and the insertion instrument functions as a cardan coupling.

2. The two part dental implant insertion system according to claim 1, wherein the round or oval protrusions of the insertion part have arched outer perimeters.

3. The two part dental implant insertion system according to claim 1, wherein the round or oval protrusions of the insertion part are globular at an upper rim of an outer perimeter of the protrusions.

4. The two part dental implant insertion system according to claim 1, wherein a stem of the insertion instrument includes a notch for clamping the insertion instrument in a machine.

5. The two part dental implant insertion system according to claim 1, wherein the insertion instrument is manually operable.

* * * * *